United States Patent

Bianchi et al.

[11] Patent Number: 5,830,679
[45] Date of Patent: Nov. 3, 1998

[54] DIAGNOSTIC BLOOD TEST TO IDENTIFY INFANTS AT RISK FOR SEPSIS

[75] Inventors: Diana W. Bianchi, Brookline; Nancy Weinschenk, Watertown, both of Mass.

[73] Assignee: New England Medical Center Hospitals, Inc., Boston, Mass.

[21] Appl. No.: 807,578

[22] Filed: Feb. 27, 1997

Related U.S. Application Data

[60] Provisional application No. 60/012,617 Mar. 1, 1996.
[51] Int. Cl.$^6$ ...................................................... G01N 33/53
[52] U.S. Cl. ...................... 435/7.24; 435/973; 436/519; 436/800; 436/811
[58] Field of Search .................................. 435/7.24, 7.92, 435/973; 436/519, 548, 800, 811

[56] References Cited

PUBLICATIONS

Coligan, J. et al. (eds), Current Protocols in Immunology, Published by National Institutes of Health, vol. II, pp. A.4.1, A.4.5, A.4.6, 1991.
Astiz et al., "Microvascular Function and Rheologic Changes in Hyperdynamic Sepsis", Critical Care Medicine 23:265–271, 1995.
Berry et al., "Premature Parturition is Characterized by In Utero Activation of the Fetal Immune System", Amer. J. of Obstetrics and Gynecology 173:1315–1320, 1995.
Birkenmaier et al., "Modulation of the Endotoxin Receptor (CD14) in Septic Patients", J. of Trauma 32:473–479, 1992.
DeLogu et al., "Serum Neopterin and Soluble Interlukin–2 Receptor for Prediction of a Shock State in Gram–Negative Sepsis", J. of Critical Care 10:64–71, 1995.
Eichacker et al., "Leukocyte CD11b/18 Antigen–Directed Monoclonal Antibody Improves Early Survival and Decreases Hypoxemia . . . Challenged with Tumor Necrosis Factor", Amer. Rev. Res. Disease 145:1023–1029, 1992.
Ridings et al., "A Dual–Binding Antibody to E–and L–Selectin Attenuates Sepsis–Induced Lung Injury", Respiratory and Critical Care Medicine 152:247–253, 1995.
Spear et al., "Soluble Interleukin–2 Receptor As A Predictor of Neonatal Sepsis", J. of Pediatrics 126:982–985, 1995.
Cecoon et al., "Immunological Markers in Neonates With Risk Factors for Early Sepsis at Different Gestational Ages," Pediatric Research, 39 (4 Part 2), p. 287A, Abstract No. 1705, Apr. 1996.
Weinschenk et al., "Activation of Leukocyte Cell Surface Markers in Neonatal Sepsis." Pediatric Research, 39 (4 Part 2), p. 292A Abstract No. 1739, Apr. 1996.
Weirich et al., "CD11b Expression on Granulocytes as a Diagnostic Marker for Neonatal Sepsis." Pediatric Research, 39 (4 Part 2), p. 303A, Abstract No. 1805, Apr. 1996.

*Primary Examiner*—Carol A. Spiegel
*Attorney, Agent, or Firm*—Fish & Richardson P.C.

[57] ABSTRACT

Disclosed is a method of diagnosing sepsis in a human infant. The method includes detecting an increase in the expression of leukocyte cell surface antigens in a blood sample from an infant at risk for developing sepsis.

8 Claims, 2 Drawing Sheets

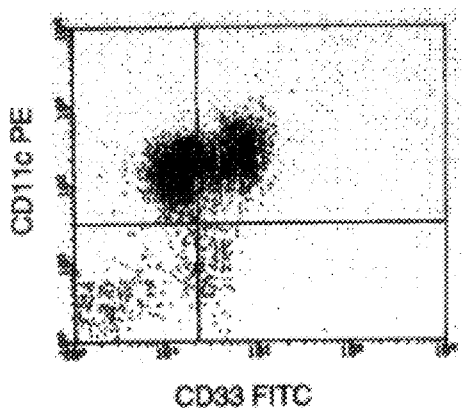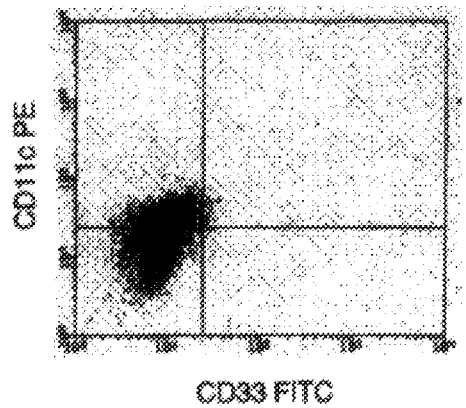
SICK
FIG. 1A
CONVALESCENT
FIG. 1B

DIAGNOSTIC BLOOD TEST TO IDENTIFY INFANTS AT RISK FOR SEPSIS

CROSS REFERENCE TO RELATED APPLICATIONS

This application claims priority from provisional application Ser. No. 60/012,617, filed Mar. 1, 1996.

FIELD OF THE INVENTION

This invention relates to pediatrics, neonatology, and disease diagnosis.

BACKGROUND OF THE INVENTION

Human neonatal sepsis can be caused by various pathogens, including Group B Streptococci, E. coli, Listeria, and viruses. Diagnosis of neonatal sepsis is typically through a sepsis workup. That involves drawing neonatal blood and performing a bacterial cell culture and complete neonatal blood cell count.

There are several disadvantages associated with a conventional neonatal sepsis workup. First, the blood volume that can be drawn from an infant for testing is typically 5–10 times smaller than the blood volume drawn from an adult. Second, if the mother has been undergoing antibiotic treatment, the baby's bacterial culture can be negative, even if bacteria are present. Third, a conventional sepsis workup takes up to two or three days. Therefore, antibiotic therapy for the infant is normally begun before the sepsis test results are available, and the therapy normally lasts for at least three days. Therefore, large numbers of infants who do not have sepsis receive antibiotic therapy anyway.

Administration of antibiotics to infants who do not actually need them is undesirable for at least two reasons. First, there are risks to the infant associated antibiotic therapy, e.g., drug allergy, hearing loss, or damage to internal organs because the drug fails to clear. Second, such use of antibiotics can contribute to the development of antibiotic resistant strains of bacteria.

SUMMARY OF THE INVENTION

We have discovered that antigens associated with leukocyte activation exhibit increased expression on the leukocyte cell membrane in a septic infant in comparison to expression of the same antigens on the leukocyte cell membrane in the same infant after recovery.

Based on this discovery, the invention features a method for detecting sepsis in a human infant patient. The method includes the steps of: (1) obtaining a blood sample from a human infant patient born to a mother having at least one infant sepsis risk factor, or an infant patient displaying at least one sign of infection; (2) contacting blood cells from the blood sample with a labelled antibody directed against a leukocyte cell surface antigen; (3) removing the leukocytes from unbound labelled antibody; (4) determining the percentage of leukocytes carrying the labelled antibody on their surface; (5) comparing the percentage of human infant patient leukocytes carrying the labelled antibody on their surface to a predetermined percentage of non-septic human infant leukocytes carrying the labelled antibody, thereby detecting an increase in leukocyte cell surface antigen expression as an indication of sepsis in the human infant patient. Preferably, the antibody is monoclonal.

The percentage of human infant patient leukocytes carrying the labelled monoclonal antibody on their surface can be determined by means of conventional flow cytometry. The flow cytometer is typically used in conjunction with a computer and software for data analysis. Preferably, red blood cells in the blood sample are lysed without lysing the leukocytes. Preferably, the leukocytes are treated with a fixative before determination of leukocytes carrying the labelled monoclonal antibody on their surface.

The normal level of expression for a given CD antigen is predetermined by obtaining data from non-septic human infants at a comparable gestational age and/or postnatal age, using the same procedure and the same monoclonal antibody used to test the human infant patient. Preferably, a panel of monoclonal antibodies is used, so that increases in the levels of expression of a multiplicity of leukocyte cell surface antigens are detected. Preferably, the monoclonal antibody is detectable by means of a fluorescent label.

As used herein, the term "normal level" of expression for a given CD antigen means the mean level of expression for that CD antigen in a population of non-septic human infants, plus or minus 10% of the mean, or plus or minus two standard deviations from the mean.

Other features and advantages of this invention will be apparent from the following detailed description of preferred embodiments thereof, and from the claims.

BRIEF DESCRIPTION OF THE DRAWINGS

FIG. 1A is a flow cytometry dot plot. It shows data on binding of PE-labelled anti-CD11c and FITC-labelled anti-CD33 to leukocytes from a neonatal patient during sepsis. The X axis is log fluorescence of CD33, the Y axis is log fluorescence of CD11c. Each dot represents a granulocyte. Cells above the horizontal line fluoresce positive for CD11c. Cells to the right of the vertical line fluoresce positive for CD33. The PC LYSIS™ software calculates the percentage of cells in each quadrant. FIG. 1A shows that during the acute illness, a large population of cells expressing CD11c and CD33 is found.

FIG. 1B is a flow cytometry dot plot. It shows data on binding of PE-labelled anti-CD11c and FITC-labelled anti-CD33 to leukocytes from the neonatal patient described in FIG. 1A after recovery from sepsis. The X axis is log fluorescence of CD33, the Y axis is log fluorescence of CD11c. Each dot represents a granulocyte. Cells above the horizontal line fluoresce positive for CD11c. Cells to the right of the vertical line fluoresce positive for CD33. The PC LYSIS™ software calculates the percentage of cells in each quadrant. FIG. 1B shows that after the acute illness, the population of cells expressing CD11c and CD33 is reduced.

DETAILED DESCRIPTION

Figure 2:
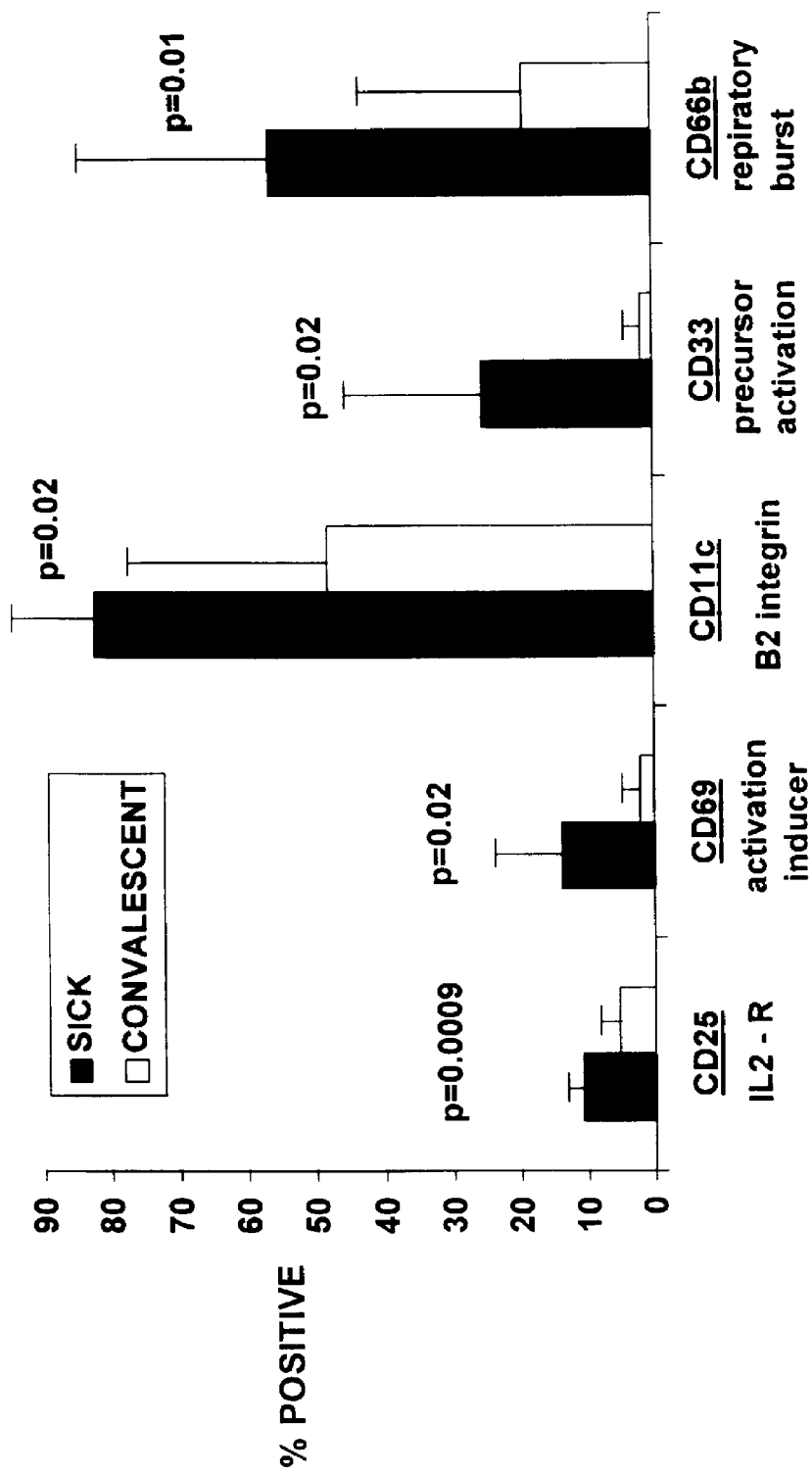
FIG. 2 is a bar graph showing the relative levels of expression of selected CD antigens in the same patient, during and after sepsis. On this bar graph, the Y axis represents the percentage of cells fluorescing positive for the antigen. The X axis is the CD antigen of interest. The stippled bars display the sick blood specimen and the clear bars, the convalescent blood sample. The lymphocyte markers CD25 (the interleukin 2 receptor), and CD69 (the activation inducer molecule) are significantly elevated during the acute illness when compared to the convalescent sample. Also, expression of the granulocyte/monocyte markers CD11c(a B2 integrin adhesion molecule), CD33 (which activates leukocyte precursors), and CD66b (which contributes to the neutrophil respiratory burst) are significantly elevated over the convalescent phase sample as measured by a two-tailed T test.

The present invention provides a simple, rapid and effective method for detection of sepsis in a human infant. The method is based on a positive correlation between sepsis and increased expression of certain leukocyte cell surface antigens associated with leukocyte activation in the infant. In general, the invention relates to a blood test involving incubation of a sample of a patient's blood cells with a monoclonal antibody or a panel of labelled monoclonal antibodies directed against certain leukocyte cell surface antigens. The method of this invention is not a test for the presence of any particular pathogen. In effect, it is a test to assess the status of the human infant patient's immune system. Therefore, the test is useful for detecting sepsis generally, regardless of the invading pathogen's identity.

As hematopoietic cells mature, they express membrane glycoproteins which participate in many cell functions, including the immune response. Previously named by their function, these molecules are now classified as CD antigens (cluster of differentiation). More than 100 CD antigens are now known and described in the literature. Their functions include: signal transduction, enzymatic functions, receptors for inflammatory mediators and immunoglobins, cell-to-cell communication, cellular adhesion and migration, and recognition of foreign versus self antigens.

The expression levels of certain CD antigens correlate significantly and usefully with sepsis in human infants, and the expression levels of other CD antigens do not. Examples of CD antigens whose expression shows a useful (positive) correlation with sepsis in human infants are: CD25 (IL-2 receptor alpha chain), CD69 (activation inducer molecule), CD11c ($B_2$ integrin alpha subunit), CD33 (activation marker on granulocyte and monocyte precursors), and CD66b (also known as CD67; augments respiratory burst activity of neutrophils). Examples of CD antigens whose expression is not usefully correlated with sepsis in human infants are: CD3 (T cell receptor), CD19 (B cell receptor), CD13 (aminopeptidase-N), and CD15 (Lewis X blood group).

According to this invention, expression levels of CD antigens on cells from patients being tested and on cells from non-septic infants used for baseline studies, are determined using conventional methods and materials. Preferred methods for determining expression levels of CD antigens are conventional monoclonal antibody binding methods. Monoclonal antibodies useful in practicing this invention are commercially available. Preferably, each monoclonal antibody is labelled with fluorescent dye. Suitable fluorescent dyes are well-known and commercially available. Particularly preferred fluorescent dyes are fluorescein isothiocyanate ("FITC") and phycoerythrin ("PE"). Methods for covalent attachment of fluorescent dyes to antibodies are well known, and all of the necessary reagents are commercially available.

To detect sepsis in a human infant patient according to this invention, a blood sample must be obtained from the human infant patient. This is done using conventional methods and materials well known to those trained in pediatric medicine or pediatric nursing. Preferably, the size of the blood sample is between 200 ul and the maximum amount drawn according to standard medical practice, taking into account the size, and age of the infant, and any other relevant factors. A blood sample size less than or greater than 200 ul can be used, depending on the requirements of the particular antibody reaction protocol followed and the type of equipment used to determine the percentage of leukocytes carrying bound, labelled monoclonal antibody.

A blood sample from a human infant patient should be obtained for testing according to the present invention as soon as the infant is born, when the mother is known to have clinical risk factors for neonatal sepsis. Maternal risk factors include maternal fever, fetal tachycardia, rupture of the amniotic membrane more than 12 hours before delivery, foul smelling amniotic fluid, uterine tenderness, increased white blood cell count, and meconium stained amniotic fluid.

If a maternal risk factor is not known to be present, a human infant patient blood sample should be obtained as soon as an infant displays signs of infection. Signs of infant infection are well known to those trained in pediatric medicine or pediatric nursing. Signs of infant infection include evidence of respiratory distress, apnea, petechiae (microbruises under the skin), irregular heart beat, rapid breathing, tachypnea, bulging anterior fontenelle, low blood sugar, and low core temperature.

The normal level of expression of leukocytes cell surface antigens measured in the practice of this invention depends on combined consideration of gestational age and post natal age. Therefore, normal base line values used in comparisons in the practice of this invention should be based on data from non septic human infants whose gestational age, or post natal age, or both, are comparable to the gestational age, post natal age, or both in the human infant patient being tested for sepsis.

Collection of normal baseline data for CD antigens whose expression increases as an indication sepsis is done in accordance with the guidance set forth herein, using conventional leukocyte/antibody binding reagents and techniques, conventional analytical techniques, e.g., flow cytometry, and well-known methods of statistical analysis. Guided by the present disclosure, collection of normal baseline data can be carried out routinely by one of ordinary skill in the art.

This invention can be carried out using a single species of monoclonal antibody directed against a single leukocyte cell surface antigen. Preferably, however, the invention is carried out using a panel of monoclonal antibodies, so that the expression level of at least two leukocyte cell surface antigens is assessed. Preferably, a panel of monoclonal antibodies includes from two to six monoclonal antibodies. One of ordinary skill in the art will recognize that the reliability of the test increases if more than one antibody is used. However, the marginal increase in reliability associated with each additional antibody used decreases as the total number of antibodies used increases.

Cells from a patient blood sample can be tested for binding to different antibodies directed against different CD antigens by successively testing each antibody individually using an aliquot of the blood cells. Alternatively, a multiplicity of monoclonal antibodies can be used simultaneously. When more than one monoclonal antibody is used simultaneously, each monoclonal antibody must be distinguishable from every other monoclonal antibody present, by means of differential labeling. Preferably, antibodies are used in pairs, so that only two differently colored fluorochromes are necessary. A preferred pair of differently-colored fluorochromes consists of FITC and PE.

Experimental Information

Blood samples (200 ul) were obtained from discarded blood specimens and the remainder of the hematology specimen at the time a CBC and blood culture were ordered. "Sick" blood specimens were obtained when the neonate received a sepsis evaluation, and subsequently had a positive blood culture or was ill appearing with signs of sepsis and received a full course of antibiotics. "Convalescent" samples were drawn (4 to 20 days later) when a subsequent surveillance CBC and blood culture were obtained.

Whole blood (50 ul) was incubated with 10 ul of antigen specific fluorescently stained monoclonal antibody. Red blood cells were lysed. Cells were fixed with paraformaldehyde.

Analysis by flow cytometry was performed using PC LYSIS II™ software (Becton-Dickinson, San Jose, Calif.) to identify the population of mononuclear cells expressing antigens, manifested by fluorescence.

A total of 8 patients were studied with an average gestational age of 25.3 weeks. Four of the sick samples were obtained at birth. The four other samples were obtained in ill appearing infants during the course of their hospitalization. Three of these infants had positive blood cultures. Three infants had necrotizing enterocolitis with negative blood cultures. Two infants were treated for presumed sepsis with negative blood cultures.

Leukocyte cell differentiation antigens are expressed on the leukocyte cell membrane during activation as part of the inflammatory response.

The purpose of this study was to evaluate the immune response in septic premature neonates. Paired blood samples from the same individual while sick and convalescent were examined to quantify the expression of leukocyte antigens in these two clinical states.

Mononuclear blood cells from eight premature infants (24 to 28 weeks gestation) were analyzed. Four infants had blood culture proven sepsis; four infants had clinical exam findings and laboratory data consistent with sepsis and received 7–14 days antibiotics despite negative cultures. The "sick" samples were drawn at the time of septic work-up; "convalescent" samples were drawn 4–20 days later. Samples were incubated with monoclonal antibodies to a T cell antigen (CD3), B cell antigen (CD19), lymphocyte antigens (CD25 and CD69), and granulocyte antigens (CD11c, CD33, and CD66b), lysed, fixed, and analyzed by flow cytometry using PC Lysis II software.

with a 575/26 band pass filter. Electronic compensation was used between fluorescence channels to remove spectral overlap. Samples were gated on forward scatter versus side-scatter to exclude debris and cell aggregates. FITC and phycoerythrin emissions were collected with a log amplifier, and immunofluorescence data were displayed on a four-decade logarithmic scale. Results were expressed as a percentage of cells staining with the antibody. Percentage of nonspecific background staining with mouse $IgG_1$ was subtracted from the total.

Other embodiments of the invention are within the following claims.

We claim:

1. A method for detecting sepsis in a human infant patient, said method comprising the steps of:
    (a) obtaining a blood sample from a human infant patient born to a mother having at least one infant sepsis risk factor, or a human infant patient displaying at least one sign of infection;
    (b) contacting leukocytes in the blood sample with a labelled antibody which specifically binds a cell surface antigen of said leukocytes, wherein said cell surface antigen is selected from the group consisting of CD25, CD69, CD11c, CD33, and CD66b;
    (c) determining the percentage of said leukocytes which bind said labelled antibody; and

TABLE 1

| | Mean % Positive (±SD) [8 infants] | | | | | | |
|---|---|---|---|---|---|---|---|
| | CD3 | CD19 | CD11c | CD25 | CD33 | CD66b | CD69 |
| Sick | 60.0 ± 10.3 | 15.4 ± 6.9 | 82.3 ± 12.2 | 10.7 ± 1.1 | 25.4 ± 20 | 56.4 ± 28.2 | 13.8 ± 9.8 |
| Convales | 49.6 ± 18.6 | 20.2 ± 15.7 | 48.2 ± 29.1 | 5.3 ± 2.6 | 1.6 ± 2.5 | 19.1 ± 24.3 | 2.1 ± 1.1 |
| Difference | p = 0.19 | p = 0.43 | p = 0.02 | p = 0.0009 | p = 0.016 | p = 0.013 | p = 0.016 |

The results in Table 1 show that cell surface antigens associated with cellular activation (CD11c, 25, 33, 66b, and 69) became significantly elevated in septic infants during the acute illness, as analyzed by a 2 tailed t test. Although these antigens are elevated at birth, the elevation seen in the septic infants was greater than expected from delivery alone. The percentage of circulating B and T cells (represented by CD19 and CD3), however, did not significantly differ in this group. With these encouraging results, we are continuing to investigate the usefulness of these antigens in the prospective evaluation of septic infants.

Flow Cytometry Sample Preparation

Monoclonal antibodies (5 $\mu$l each) were added to each sample. Samples were incubated with antibody for 45 minutes on ice, centrifuged, washed twice with 500 $\mu$l of the 0.5% BSA-PBS mixture, and centrifuged again. Each aliquot of the patient's sample was resuspended in 1 ml of lysis buffer (960 $\mu$l PBS plus 40 $\mu$l Immuno-lyse, Coulter Corp., Miami, catalog No. 6602490), and mixed in a vortex agitator. Immediately afterward, 200 $\mu$l of fixative (Coulter catalog No. 6604470) was added. The samples were then mixed in a vortex agitator, centrifuged, and washed once more with BSA-PBS. Before fluorescence-activated cell sorter analysis, each sample was resuspended in 250 $\mu$l PBS.

Fluorescence-Activated Cell Sorter Analysis

Samples were analyzed on a Becton-Dickinson fluorescence-activated cell sorter Vantage model flow cytometer equipped with Lysis II acquisition and analysis software. FITC emission was detected with a 530/30 nm band pass filter, and phycoerythrin emission was detected (d) comparing the percentage of leukocytes which bind said labelled antibody to the percentage of leukocytes which bind said labelled antibody in a blood sample from a non-septic human infant age-matched to said human infant patient, wherein an increased percentage in the human infant patient compared to the non-septic human infant indicates sepsis in the human infant patient.

2. The method of claim 1, wherein said labelled antibody is a monoclonal antibody.

3. The method of claim 1, wherein said determining step comprises flow cytometry.

4. The method of claim 1, wherein red blood cells in said blood sample are lysed after contacting said blood sample with said labelled antibody without lysing said leukocytes.

5. The method of claim 1, wherein said leukocytes are treated with a fixative before determination of leukocytes with the labelled antibody bound on their surface.

6. The method of claim 1, wherein said contacting step further comprising contacting said blood sample with a second labelled antibody which specifically binds to a different said cell surface antigen, wherein the two labelled antibodies are labelled with different labels.

7. The method of claim 1 wherein the antibody is labelled with a fluorescent dye.

8. The method of claim 7 wherein the fluorescent dye is fluorescein isothiocyanate or phycoerythrin.

* * * * *